United States Patent [19]
Parker

[11] Patent Number: 5,845,634
[45] Date of Patent: Dec. 8, 1998

[54] ENDOSCOPE VIEWING SYSTEM WITH OROTRACHEAL INTRODUCING GUIDE

[75] Inventor: Jeffrey D. Parker, Cincinnati, Ohio

[73] Assignee: Parker Medical Limited Partnership, Cincinnati, Ohio

[21] Appl. No.: 819,782

[22] Filed: Mar. 18, 1997

[51] Int. Cl.[6] .................................................. A61M 16/00
[52] U.S. Cl. ............................. 128/200.26; 128/207.14; 600/103; 600/153
[58] Field of Search .................... 128/207.14, 200.26, 128/201.26, 207.18, 207.15, 911, 912; 600/102, 109, 153, 156, 169, 175, 178

[56] References Cited

U.S. PATENT DOCUMENTS

| | | | |
|---|---|---|---|
| 4,809,680 | 3/1989 | Yabe | 600/109 |
| 5,024,218 | 6/1991 | Ovassapian et al. | 128/200.26 |
| 5,035,231 | 7/1991 | Kubokawa et al. | 600/109 |
| 5,042,469 | 8/1991 | Augustine | 128/200.26 |
| 5,193,544 | 3/1993 | Jaffe | 128/207.14 |
| 5,339,805 | 8/1994 | Parker | 128/207.14 |
| 5,400,771 | 3/1995 | Pirak et al. | 128/200.26 |
| 5,533,496 | 7/1996 | De Faria-Correa et al. | 600/169 |
| 5,605,532 | 2/1997 | Schermerhorn | 600/169 |

*Primary Examiner*—John G. Weiss
*Assistant Examiner*—V. Srivastava
*Attorney, Agent, or Firm*—Wood, Herron & Evans L.L.P.

[57] ABSTRACT

An endoscope viewing system including an orotracheal introducing guide (10) having channels (60) therethrough to support endoscope imaging end components (70,72) and, if desired, medical implements (120).

18 Claims, 4 Drawing Sheets

ENDOSCOPE VIEWING SYSTEM WITH OROTRACHEAL INTRODUCING GUIDE

BACKGROUND OF THE INVENTION

I. Field of the Invention

The present invention relates to endoscope viewing systems and more particularly to such viewing systems useful with orotracheal intubation guides.

II. Description of Prior Art

When a patient stops breathing it is imperative that effective ventilation be instituted as soon as possible. Ventilation is best accomplished by forcing air through an orotracheal tube inserted through the mouth and laryngeal opening and into the trachea. A commonly employed method of orotracheal intubation relies on a blade laryngoscope which is used to allow the medical practitioner to visualize the laryngeal opening and insert the tube. Intubation with the blade laryngoscope presents significant difficulties and risks. In addition to possible injury or trauma to the patient in the utilization of the blade laryngoscope, it is not uncommon for the orotracheal tube to be accidentally inserted into anatomical spaces surrounding the larynx, such as the closely adjacent esophagus. Such misintubation, if not quickly recognized and corrected, may have fatal consequences.

Another approach to intubation is so-called blind intubation in which an intubation guide is inserted into the throat to guide the orotracheal tube into the laryngeal opening without requiring visualization of the laryngeal opening. I have developed blind intubation guides which both minimize injury and trauma in use, and also substantially reduce the risk of misintubation. Such intubation guides are shown, for example, in my U.S. Pat. No. 5,339,805, and my U.S. Patent Application entitled "Orotracheal Intubation Guide", filed concurrently herewith. The disclosures of my aforesaid '805 patent and concurrently-filed patent application are both incorporated herein by reference in their entireties.

As shown in my aforesaid patent and application, my blind intubation guides provide a tube-guiding wall that is positionable in the throat adjacent the posterior edge of the laryngeal opening such that advancement of an orotracheal tube therealong will guide the tube safely and quickly into the laryngeal opening. With such blind intubation guides, positioning of the guide wall is essentially automatic so that visualization of the laryngeal opening is not necessary. In some instances, however, it may be useful to observe the orotracheal tube approaching and entering the glottis, such as where the larynx is known to be anatomically deformed or is subject to easy bleeding from minor trauma. To this end, the intubation guide of my '805 patent includes a slant tunnel extending through the body of the guide and terminating in a port in the tube-guiding wall. The distal viewing end of the typical endoscope insertion tube is inserted through the slant tunnel and positioned at the back of the throat by the guide with the proximal end of the insertion tube extending out of the mouth to a viewing end by which to visualize the larynx from outside the throat. The guide positions the distal end of the insertion tube such that the endoscope is aimed to view the posterior commissure of the glottis.

The insertion tube of the typical endoscope contains all the imaging end components (i.e., the optical, illuminating, and other distal endoscope components) in one bundle. Such an insertion tube is relatively large and requires a considerable thickness or substance of the guide body to contain the insertion tube. It is desirable to streamline the size of the intubation guide, such as I have done with the guide device shown in my aforementioned concurrently-filed application. However, with the streamlined intubation guide, the insertion tube may not readily fit within the body of the guide.

Additionally, it is desirable to utilize the ability of the intubation guide to properly locate and position other tubular instruments within the throat to facilitate other procedures within the laryngeal opening. However, the guide body has limited space and material available for other medical implements, such as suction catheters, biopsy tools or similar implements, to reach into the laryngeal opening. Indeed, the tunnel used to contain the insertion tube may consume so much of the substance of the body that there may be little room left for other medical implements.

SUMMARY OF THE INVENTION

The present invention provides a modified endoscope system that overcomes the above-mentioned drawbacks. To this end, and in accordance with the principles of the present invention, the insertion tube at the imaging end of the endoscope is eliminated. Instead, the intubation guide is provided with a plurality of channels extending through the body, such that the imaging and illuminating components of the endoscope may each be contained within a respective channel of the guide body. As a consequence, these and other components of the endoscope may be spread out through the body of the guide, rather than being lumped together in a single insertion tube as is typical of conventional endoscopes.

The channels advantageously run through the guide to openings in the tube-guiding wall wherein an objective lens may be contained to facilitate the function of the endoscope viewing system. Moreover, the endoscope imaging end components may be formed integrally within the guide body thus defining the channels therefor to be co-extensive with the components so as to eliminate the need to insert and position the endoscope components for each use. Further, the separate-component channels are each smaller than the slant tunnel of my prior guide, and so leave more substance of the body available for additional channels wherein to contain other medical implements such as for biopsy procedures and the like. Thus, the intubation guide serves both as a protective encasement and as an introducing guide for the endoscope and other medical implements.

In accordance with a further aspect of the present invention, it will be appreciated that the objective lens of the endoscope viewing system is prone to becoming fogged, especially in the throat where warm moist air may be expelled therealong. To obviate that problem, a fog reduction system may be built into the guide along with the objective lens to alter the environment of the lens thereby reducing the likelihood of fog formation thereon. The fog reduction system is advantageously provided by a heating element which extends about the channel opening containing the objective lens.

By virtue of the foregoing, there is thus provided an endoscope viewing system combined with an orotracheal introducing guide that overcomes drawbacks and limitations of prior endoscope viewing systems. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTION OF THE DRAWINGS

Figure 1:
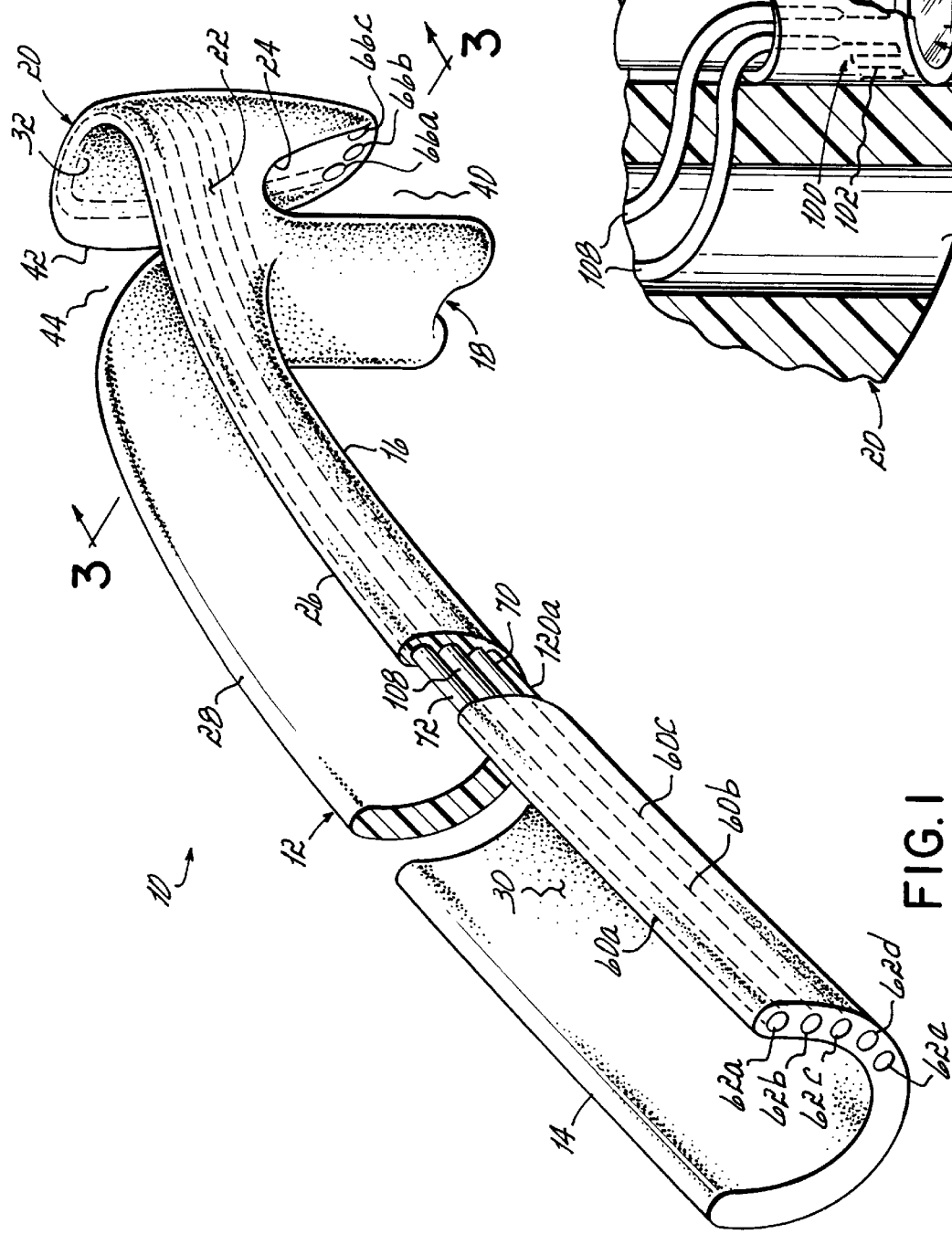
FIG. 1 is a perspective, partially broken away, right rear view of an orotracheal intubation guide adapted for endoscope viewing in accordance with the principals of the present invention.
Figure 2:
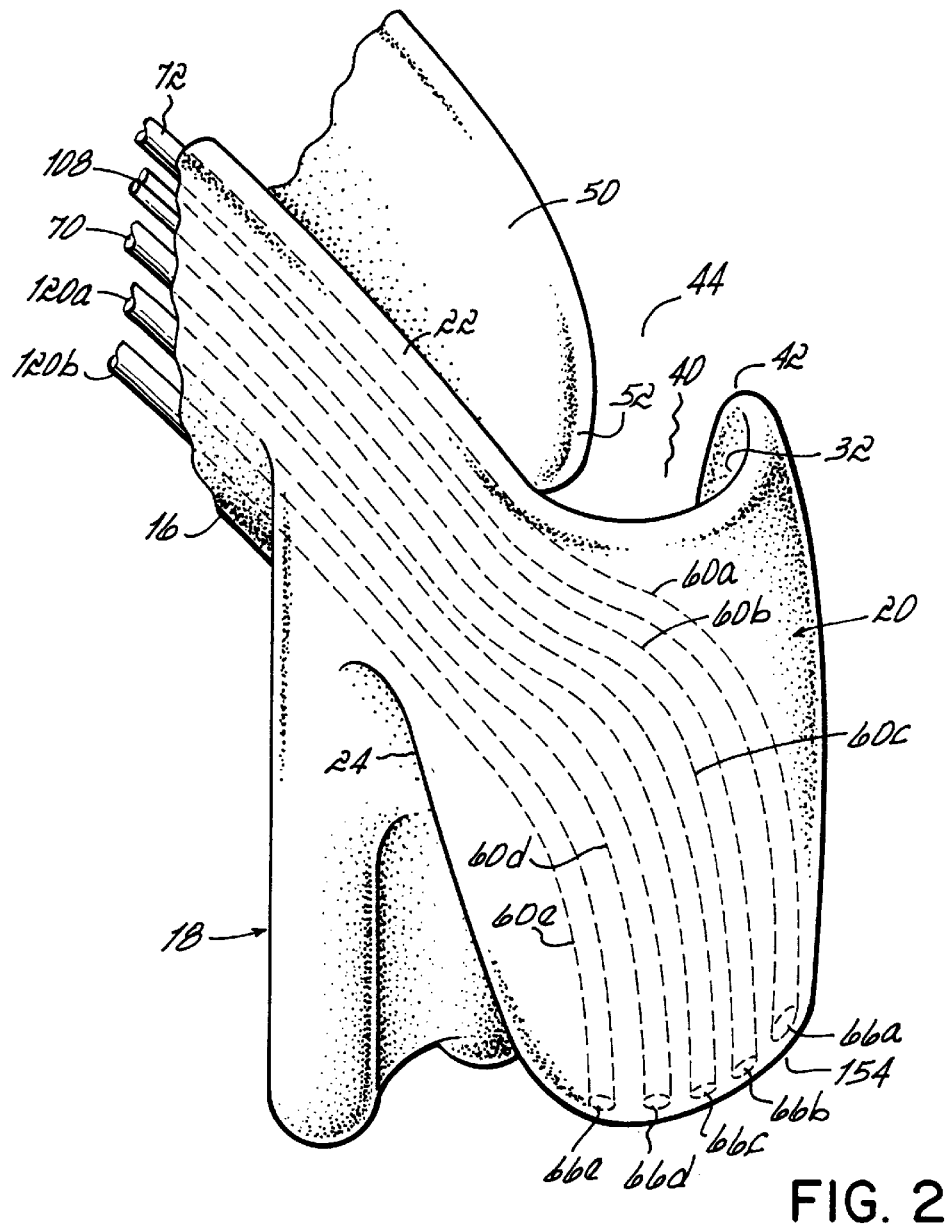
FIG. 2 is a front perspective view of the guide of FIG. 1.
Figure 3:
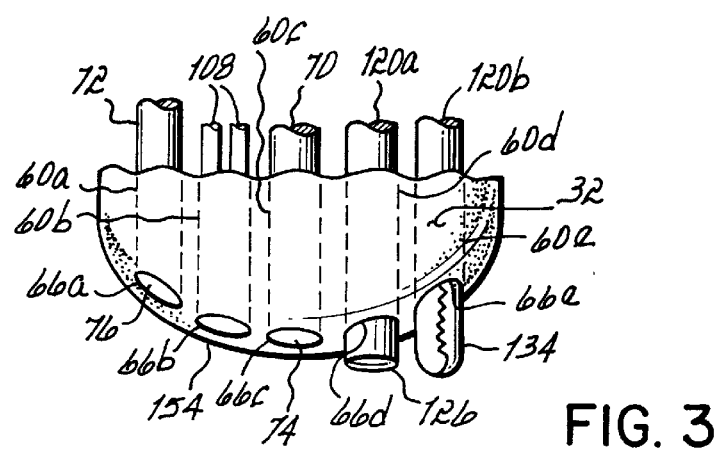
FIG. 3 is a partially broken away view taken along line 3—3 of FIG. 1.

With reference to FIGS. 1–3, there is shown an orotracheal introducing guide 10, injection molded as a single piece of plastic (e.g., polyethylene, polypropylene, or ABS) and adapted for endoscope viewing in accordance with the principals of the present invention. Guide 10 is based upon a blind intubation guide substantially as shown and described in my aforementioned concurrently-filed application, to which the reader is referred for greater details regarding the construction and use of guide 10 for blind orotracheal intubation. For present purposes, therefore, it will be appreciated that guide 10 includes a body 12 having a proximal handle portion 14, an aft tongue-depressing portion or member 16, a support portion 18 and a tube tip guide portion 20 connected to the aft member 16 and support portion 18 by a single side arm 22 (having an arcuate lower edge 24). At least aft portion 16 has a generally U-shaped cross-section or groove having opposed side walls 26 and 28, and floor 30. Side walls 26, 28 extend or merge with handle portion 14. Floor 30 may also extend or merge with handle portion 14 as desired.

Figure 6:
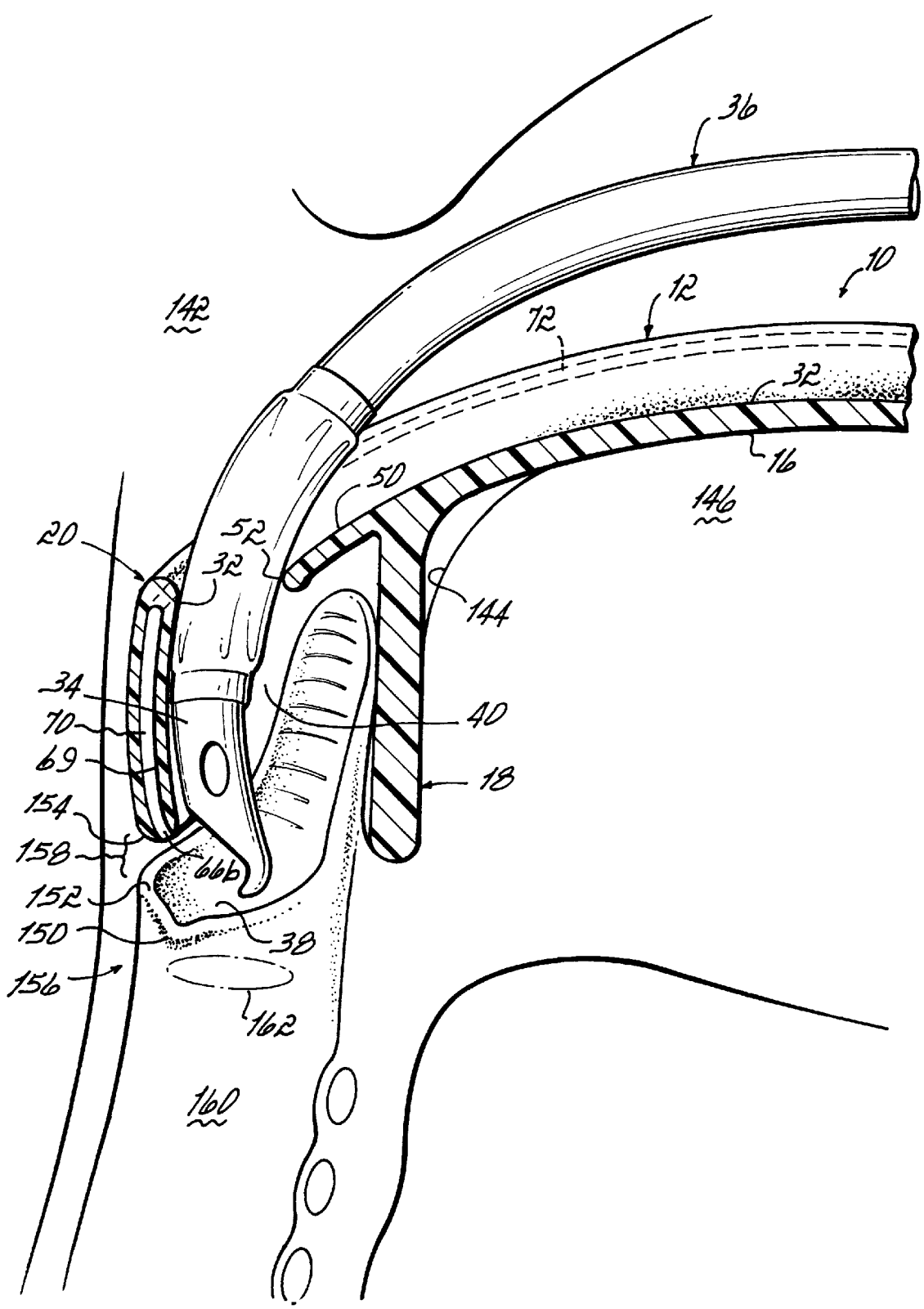
FIG. 6 is a schematic illustration, partially cut-away, showing the guide of FIG. 1 positioned in the throat for purposes of describing operation of the present invention.

Tube tip guide portion 20 has an inner tube-guiding wall 32 along which the distal end 34 of an endotracheal tube 36 is guided into a patient's laryngeal opening 38 (FIG. 6). To this end, arm 22 spaces support portion 18 and guide wall 32 apart to define a tube-receiving space 40 therebetween. The free vertical edge 42 of tube tip guide portion 20 is spaced opposite support portion 18 to define a tube-removal slot 44 therebetween. Guide 10 may further include an extended tube-support 50 which extends to a free distal edge 52 in space 40 so as to effectively define a spout that creates an overhanging eave in space 40.

Guide 10 differs from the guide of my aforementioned concurrently-filed application primarily by the inclusion of channels 60 (five shown) such as to facilitate endoscope viewing as will now be described. To this end, a plurality of generally parallel channels 60a–e extend from a respective access or entrance point 62a–e along the back edge 64 of body 12, through side wall 26, side arm 22 and tube tip guide portion 20, and terminate in respective ports 66a–e along tube-guiding wall 32. Several of the channels 60 (e.g., channels 60a–c) constitute endoscope component channels to carry the image end components of an endoscope. For example, individual channel 60c carries an image guide component 70 of an endoscope system, whereas outer channel 60b carries a light transmitter component 72 of such a system.

Figure 4:
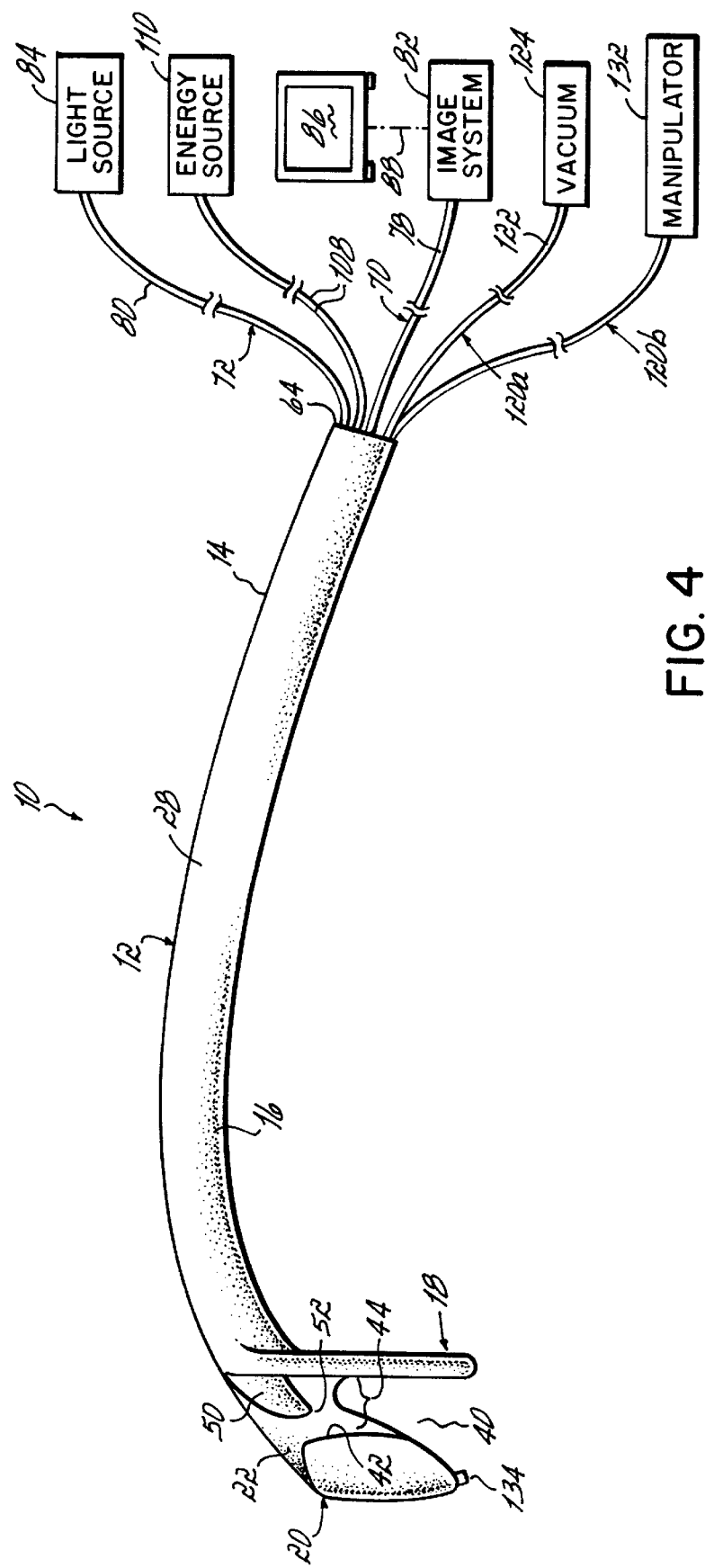
FIG. 4 is a schematic view of the guide of FIG. 1 as part of an endoscope viewing system and showing use of other medical implements.

Image end components 70 and 72 extend into channels 60a and 60b, respectively, such that the distal ends 74 and 76 thereof are adjacent ports 66c and 66b, respectively. The proximal ends 78 and 80 of components 70 and 72 extend from access points 62c and 62a to connect to a viewing system 82 and a light source 84, respectively, such as shown in FIG. 4. For these purposes, image guide component 70 may be a fiberoptic strand (or a plurality of such strands) to transmit an optical image from an objective lens 90 (FIG. 5) at the distal end 74 of component 70 positioned at port 66c to an exterior viewing system 82 such as an optical lens (FIG. 4). Alternatively, images from the objective lens at distal end 74 of image guide component 70 may be transmitted to a CCD imaging device located behind the objective lens with guide 70 defining wires to power the CCD device, and to transmit images from the CCD device to an image processing unit in viewing system 82, which processes the CCD signal for video projection on a television monitor 86 (as exemplified by the dotted line electrical connection 88 of system 82 and monitor 86 in FIG. 4). Similarly, light transmitter component 72 may be a fiberoptic strand (or a plurality of such strands) to couple light from light source 84 (FIG. 4) to distal end 76 of transmitter 72 at port 66a. In this way, the area to be viewed by image guide 70 may be illuminated via light transmitter 72. Although only one light transmitter component 72 is shown, it will be appreciated that many endoscopes employ two light transmitter components 72 in which event the second such transmitter component may either be included in channel 60a, or provided in its own further channel, the goal being to have the distal end 74 of the light transmitter component 72 aimed along with imaging component 70 to properly illuminate the viewing area.

Distal end 76 of light transmitter 72 could simply be a polished end of the fiberoptic strand(s) thereof. For imaging, however, it is desirable that a lens be provided at distal end 74 of image guide component 70. To this end, and as shown diagrammatically in FIG. 5, an objective lens 90 may be associated with port 66c. Lens 90 may be permanently associated with image guide component 70 at distal end 74 thereof and/or may be permanently imbedded into the material of guide 10 at port 66c. In either case, it will be appreciated that the objective lens 90 may have a tendency to fog up in use. To reduce or eliminate fog, it is necessary to reach lens 90 and in some way alter the environment 92 thereat.

Figure 5:
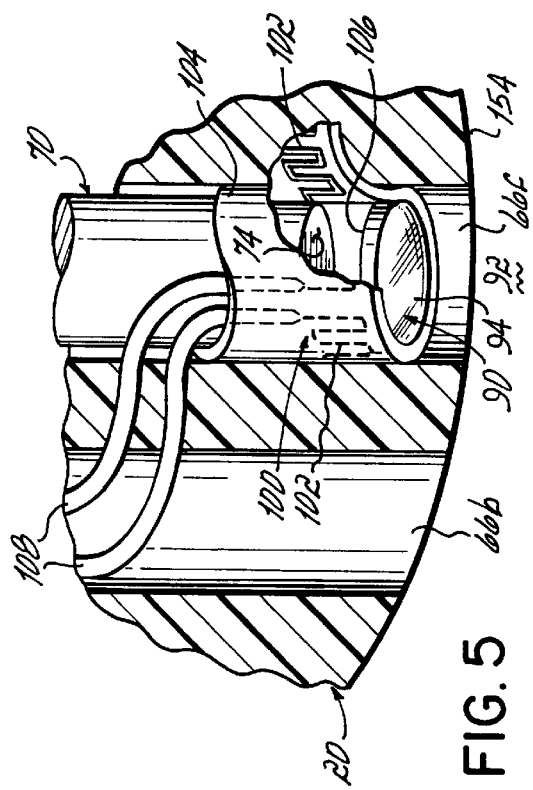
FIG. 5 is an enlarged partially cut-away view of a portion of the guide of FIG. 1 showing a heating system and objective lens for reduced-fog endoscope viewing.

Environment 92 may be suitably altered by heating the lens 90 or environment 92. For this purpose, and with further reference to FIG. 5, a heater element 100 may be associated with port 66c such that when energized, the temperature of lens 90 and/or environment 92 becomes elevated thereby substantially reducing the tendency of fog to form on lens 90. Element 100 may be provided by electrical resistance wires 102 or by a thin film heater substrate 104 (in which case wires 102 are resistive material supported on substrate 104) wrapped around distal end 74 or embedded in the material of guide 10 about port 66c. Resistance wire heating may be accomplished in the manner shown with regard to FIG. 3 of U.S. Pat. No. 5,605,532. Substrate heating may be provided by a thin film heater available from Dekko Heating Technologies, North Webster, Ind. Alternatively, lens 90 and/or environment 92 may be warmed by placing heater element 100 within lens 90 (such as by embedding a resistance wire in lens 90), or by placing element 100 against lens 90 such as by coating an optically transmissive, electrically resistive material (such as Iconel 600 or Mylar) on the backside 106 of lens 90, both as shown in FIGS. 4 and 5, respectively, of U.S. Pat. No. 5,605,532. The disclosure of U.S. Pat. No. 5,605,532 is incorporated herein by reference in its entirety.

Electrical power for heater element 100 may be provided by wires 108 coupled thereto and extending through channel 60b (or a pair of such channels if wires 108 are to be kept separate). Wires 108 extend out of access point 62b and are coupled to an energy source 110 exterior to guide 10 (FIG. 4). Port 66b may be occluded if desired. As an alternative, wires 108 may extend only partially through channel 60b to a battery (not shown) embedded within the material of guide 10 and operated with a switch (also not shown) accessible at a surface of guide 10. Moreover, the electrical heating system may be replaced with a warm air system to warm lens 90 and/or environment 92. To this end, energy source 110 may be a supply of warm air and a blower, and wires 108 may be replaced with a tube inserted into access point 62b, for example, to carry heated air from source 10 through channel 60b to be expelled at port 66b adjacent lens 90.

The size of the channels 60a–e is kept as small as possible so as to provide the minimum clearance necessary to selectively receive the endoscope components inserted into respective channels 60a–e. Alternatively, the guide 10 may be molded about various of the components such that the components therebetween substantially occupy the channel and the channel therefor closely matches to the size and shape of the component. It will thus be understood that channel as used herein is a reference to a lumen that receives a component and/or the space occupied by the component. Thus, reusable endoscope imaging end components may be utilized, or the components may be made integral with guide 10 and disposed of (or sterilized) with the guide. In the latter event, the components may extend freely from back edge 64 of guide 10, or they may terminate thereat in which event a connector (not shown) may be used to couple the endoscope components to the external elements of the endoscope.

To facilitate other medical procedures, one or more of channels 60, such as channels 60d and/or 60e, may be used to carry various medical implements 120a and b. By way of example, channel 60d may carry therein a suction catheter 120a which is attached at its proximal end 122 to a source of vacuum 124 (FIG. 4), and has its distal end 126 exposed at or beyond port 66d in the tube-guiding wall 32. Similarly, a remotely operated medical device 120b (such as a biopsy cutters or forceps) may be carried through channel 60e with the manipulator 132 external to guide 10 (FIG. 4) for operation by the surgeon (not shown) and the active end 134 exposed at or beyond port 66e.

In use, and with reference to FIG. 6, guide 10 containing at least endoscope components 70 and 72 (only component 70 shown in FIG. 6) is inserted through a patient's mouth (not shown) and into the throat 142 in the same manner as described in my aforementioned concurrently-filed application. Guide 10 is inserted until support portion 18 comes to rest at the back 144 of tongue 146. In this position, aft member 16 is supported over tongue 146 by support member 18 and tube-guiding wall 32 is situated at the back of the throat 140 in an orientation that effectively defines an upward continuation of the posterior edge 150 of the laryngeal opening 38. More particularly, for purposes of inserting orotracheal tube 36 into laryngeal opening 38, the lowermost edge 154 of guide wall 32 is generally adjacent to or contiguous with the posterior edge 150 of laryngeal opening 38 so as to prevent tube tip 34 from passing between guide wall 32 and laryngeal edge 152 into the esophagus 156 or other anatomical spaces outside the laryngeal opening. As may be seen in FIG. 6, lower edge 154 of guide wall 32 need not necessarily touch the posterior edge 150 of laryngeal opening 38 so long as they are functionally contiguous such that the gap 158 therebetween is dimensionally and/or angularly inaccessible to tube tip 34 so as to provide a pathway or trajectory for tube 36 through tube-receiving space 40 exclusively into laryngeal opening 38 and trachea 160.

With guide 10 seated in the throat of the human or animal patient, tube 36 may be inserted into laryngeal opening 38. Channels 60 and endoscope components 70 and 72 allow visualization of the tube insertion and/or for other purposes. To this end, ports 66a–e are advantageously positioned along the distal, lower edge 154 of wall 32 with the immediately inner aspect 69 of each channel 60 angled within portion 20 so as to aim from just underneath distal end 34 of tube 36 and parallel to the trajectory of tube 36 into laryngeal opening 38. In this position, the illuminating and imaging endoscope components carried by endoscope-component channels 60c and 60a are aimed to view an area forward of the components 70, 72 such as the posterior commisure of the glottis 162. Additionally, suction may be applied in that same area and/or medical procedures (such as a biopsy) may be conducted thereat with medical implements 120 carried by the medical implement channels (e.g. 60d and 60e). Also, fog which may impair the ability to view the area may be reduced or eliminated by use of the fog reduction means described herein.

By virtue of the foregoing, there is thus provided an endoscope viewing system with advantages and features not heretofore provided.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, although each channel 60 is shown as terminating into its own port 66, several of the channels could share the same opening 66, or one of ports 66 may be enlarged so as to define a single opening for several of the channels. Also, to facilitate ease of use of tube 36, the distal tip 34 may be advantageously provided with a partial posterior bevel and curved anterior lip as described in my U.S. Patent Application entitled "Endotracheal Tube" and filed concurrently herewith, the disclosure of which is also incorporated herein by reference in its entirety. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. An endoscope viewing system comprising:

an orotracheal introducing guide having a body with a tube-guiding wall and a plurality of separate endoscope-element channels extending inside through the body and terminating at an opening in the tube-guiding wall; and a light transmitting component and an image guide component of an endoscope, each endoscope component extending through a respective one of the endoscope-element channels to the opening, the light transmitting component having a distal end positioned relative to the opening to illuminate an area, the image guide component having a distal end positioned relative to the opening to receive an image from the area.

2. The endoscope viewing system of claim 1 further including a separate, medical implement channel extending through the body and terminating in an opening in the tube-guiding wall, whereby to facilitate use of a medical implement along with the endoscope.

3. The endoscope viewing system of claim 1 further comprising an objective lens associated with the opening at which the channel containing the image guide terminates.

4. The endoscope viewing system of claim 3 further comprising fog reduction means for reducing fog formation on the objective lens.

5. The endoscope viewing system of claim 3 further comprising heater means associated with the opening containing the objective lens for reducing fog formation on the objective lens.

6. The endoscope viewing system of claim 1 wherein each channel terminates into a respective, separate opening.

7. The endoscope viewing system of claim 1 wherein the channels are generally parallel to one another.

8. The endoscope viewing system of claim 1 wherein the opening is along a distal, lower edge of the tube-guiding wall.

9. The endoscope viewing system of claim 1 wherein the image guide components are integrally held within the respective endoscope-element channels.

10. An endoscope viewing system comprising:

an orotracheal introducing guide having a body, the body including an aft member, a guide portion supporting a tube-guiding wall, and a single side arm, the aft member and the guide portion being interconnected to each other by only the single side arm to define a gap opposite the single side arm and between the aft member and the guide portion;

at least a light transmitting component and an image guide component of an endoscope;

a plurality of endoscope-element channel means extending through the aft member, guide support and single side arm and terminating in an opening along the tube-guiding wall for carrying respective ones of the endoscope components therein, the light transmitting component having a distal end positioned relative to the opening of the channel means to illuminate an area, the image guide component having a distal end positioned relative to the opening of the channel means to receive an image from the area.

11. The endoscope viewing system of claim 10 further including a separate, medical implement channel extending through the aft member, guide support and side arm and terminating at an opening in the tube-guiding wall, whereby to facilitate use of a medical implement along with the endoscope.

12. The endoscope viewing system of claim 10 further comprising an objective lens associated with the opening at which the channel means containing the image guide terminates.

13. The endoscope viewing system of claim 12 further comprising fog reduction means for reducing fog formation on the objective lens.

14. The endoscope viewing system of claim 12 further comprising heater means associated with the opening containing the objective lens for reducing fog formation on the objective lens.

15. The endoscope viewing system of claim 10 wherein each channel means terminates into a respective, separate opening.

16. The endoscope viewing system of claim 10 wherein the channel means are generally parallel to one another.

17. The endoscope viewing system of claim 10 wherein the opening is along a distal, lower edge of the tube-guiding wall.

18. The endoscope viewing system of claim 10 wherein the image guide components are integrally held within the respective endoscope-element channel means.

\* \* \* \* \*

UNITED STATES PATENT AND TRADEMARK OFFICE
CERTIFICATE OF CORRECTION

PATENT NO.   : 5,845,634

DATED        : December 8, 1998

INVENTOR(S)  : Jeffrey D. Parker

It is certified that error appears in the above-identified patent and that said Letters Patent is hereby corrected as shown below:

On the title page: Item [56]
add the following to the list of "References Cited":

--4,076,018    2/1978    Heckele . . .
  4,279,246    7/1981    Chikama . . .
  5,448,990    9/1995    De Faria-Correa . . .

FOREIGN PATENT DOCUMENTS 2293180        7/1976    France.
WO89/02719     4/1989    WTPO.

OTHER DOCUMENTS

International Search Report, PCT/US98/04783, mailed July 19, 1998.--

Column 5, line 21, please delete "source 10" and replace with --source 110--.

Signed and Sealed this

Fifth Day of October, 1999

*Attest:*

*Attesting Officer*

Q. TODD DICKINSON

*Acting Commissioner of Patents and Trademarks*